(12) United States Patent
Williams et al.

(10) Patent No.: US 6,264,328 B1
(45) Date of Patent: Jul. 24, 2001

(54) WAVEFRONT SENSOR WITH OFF-AXIS ILLUMINATION

(75) Inventors: David R. Williams, Fairport; Geun-Young Yoon, Rochester, both of NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/422,338

(22) Filed: Oct. 21, 1999

(51) Int. Cl.[7] .................................................. A61B 3/10
(52) U.S. Cl. ................................................ 351/221
(58) Field of Search ..................... 351/205, 206, 351/214, 221, 211, 219, 246, 247

(56) References Cited

U.S. PATENT DOCUMENTS

| | | |
|---|---|---|
| 4,991,953 * | 2/1991 | Pflibsen et al. ................ 351/206 |
| 5,663,781 | 9/1997 | Wilms et al. . |
| 5,777,719 | 7/1998 | Williams et al. . |

FOREIGN PATENT DOCUMENTS

| | | |
|---|---|---|
| 42 22 395 A1 | 1/1994 | (DE) . |
| 0691103 | 1/1996 | (EP) . |

OTHER PUBLICATIONS

Liang, et al., "Objective Measurement of Wave Aberrations of the Human Eye With the Use of a Hartmann–Shack Wave–front Sensor", *J. Opt. Soc. Am. A.*, vol. 11, No. 7, pp. 1–9, (Jul. 1994).

* cited by examiner

*Primary Examiner*—George Manuel
(74) *Attorney, Agent, or Firm*—Blank Rome Comisky & McCauley LLP

(57) ABSTRACT

Wavefront aberrations in an eye are detected by illuminating the retina, receiving the light reflected by the retina and using a Hartmann-Shack detector or the like to detect the aberrations. The illuminating light is applied to the eye off of the optical axis of the eye. Light reflected from the cornea and light reflected from the retina travel in different directions. The former can be blocked with a stop, while the latter is passed to the detector.

20 Claims, 3 Drawing Sheets

WAVEFRONT SENSOR WITH OFF-AXIS ILLUMINATION

BACKGROUND OF THE INVENTION

The present invention is directed to a wavefront sensor, such as a sensor for wavefront aberrations in the eye, and more particularly to such a sensor which avoids corneal reflection by illuminating the retina along a light path off of the optical axis of the eye. The present invention is further directed to a method of sensing a wavefront using such off-axis illumination.

It is known in the art to detect wavefront aberrations in the human eye for such purposes as intraocular surgery and contact lens fabrication. Such detection is disclosed, e.g., in Liang et al, "Objective measurement of wave aberrations of the human eye with the user of a Hartmann-Shack wavefront sensor," *Journal of the Optical Society of America*, Vol. 11, No. 7, July, 1994, pp. 1–9. A beam of light from a laser diode or other light source is directed toward the pupil and is incident on the retina. Because the retina is highly absorbing, a beam on the order of four orders of magnitude dimmer than the original beam is reflected by the retina and emerges from the pupil. Typically, the incoming and emergent light follow a common optical path; the incoming light is brought into the common optical path with a beamsplitter.

The emergent beam is applied to a Hartmann-Shack detector to detect the aberrations. Such a detector includes an array of lenslets which break up the light into an array of spots and focus the spots onto a charge-coupled detector or other two-dimensional light detector. Each spot is located to determine its displacement from the position which it would occupy in the absence of wavefront aberrations, and the displacements of the spots allow reconstruction of the wavefront and thus detection of the aberrations.

Improvements to the technique of Liang et al are taught in J. Liang and D. R. Williams, "Aberrations and retinal image quality of the normal human eye," *Journal of the Optical Society of America*, Vol. 4, No. 11, November, 1997, pp. 2873–2883 and in U.S. Pat. No. 5,777,719 to Williams et al. Williams et al teaches techniques for detecting aberrations and for using the aberrations thus detected for eye surgery and the fabrication of intraocular and contact lenses. Moreover, the techniques of those references, unlike that of the Liang et al 1994 article, lend themselves to automation.

The techniques described above involve illuminating the eye along the eye's optical axis. As a consequence, the light reflected from the retina is mixed with stray reflections which can disrupt measurements. More specifically, the stray reflections show up as spurious bright spots amid the array of spots formed in the Hartmann-Shack sensor.

Such stray reflections have several sources in wavefront sensors. Of particular concern are the reflections from the optical elements between the retina and the beamsplitter. Such elements typically include the optics of the eye and a pair of lenses between the beamsplitter and the eye. Back reflections from surfaces other than the retina are weak relative to the illuminating beam but are bright relative to the weak signal reflected from the retina.

In the eye's optics, the only surface whose back reflection is bright enough to be problematic is the first (outer) surface of the cornea. That reflection is comparable in energy to the reflection from the retina and can therefore be a considerable nuisance for wavefront sensing, particularly if the centroids of the spots in the detector are to be computed automatically.

One known way to remove the corneal reflection, taught in Liang and Williams and in Williams et al, uses a polarizing beamsplitter to remove reflected light from all of the surfaces between the beamsplitter and the retina. Because those surfaces retain the linear polarization of the light incident thereon, both lens reflections and the corneal reflection are eliminated. However, much of the light reflected from the retina is also lost. Only depolarized light reflected from the retina, which accounts for only about thirty percent of the total light reflected from the retina, is available to detect the wavefront aberration. Moreover, the depolarized light contains considerable spatial noise. Still another problem is the intensity nonuniformity introduced into the array of spots by the birefringence of the eye's optics, chiefly the cornea.

Another known way to remove reflections from all optics between the beamsplitter and the eye while increasing the signal from the retina involves the use of a polarizing beamsplitter in combination with a quarter-wavelength ($\lambda/4$) plate just in front of the eye. German published patent application No. DE 42 22 395 A1 teaches that technique. That technique allows a much greater part of the light reflected from the retina to reach the detector, thereby improving spot quality, while removing the variation in spot brightness caused by the birefringence of the eye. It also removes back reflection from the lenses. However, the corneal reflection is not removed and is thus just as troublesome as it would be in the absence of polarizing optics.

Another problem with the two techniques just described is the cost of the polarizing beamsplitter and of the $\lambda/4$ plate. In cost-sensitive commercial settings, it would be desirable to eliminate that cost.

SUMMARY OF THE INVENTION

In light of the foregoing, it will be readily apparent that a need exists in the art to provide a wavefront sensor in which the corneal reflection does not cause spurious spots on the detector or otherwise degrade the signal derived from the light reflected from the retina. More particularly, there is a need to detect wavefront aberrations in an accurate and cost-effective manner by eliminating the problem of corneal reflection without using polarizing optics.

It is therefore an object of the invention to address those needs.

To achieve the above and other objects, the present invention is directed to a wavefront sensor in which the eye is illuminated off-axis. The light not reflected by the cornea impinges on the retina, and the light reflected by the retina returns through the lens and the cornea. That light is thereby focused into an optical path different from the optical path followed by the corneal reflection. The entire retinal reflection is used, and the corneal reflection can be discarded by use of simple, inexpensive, non-polarizing optics such as a stop.

The beam used to illuminate the eye is relatively narrow, e.g., around 1–1.5 mm in diameter, and intersects the cornea in a small area, thus further reducing the probability that the corneal reflection will take a return path to the detector. In addition, the dioptric range over which the small spot is in focus on the retina can be increased. Typically, a displacement of the illuminating beam from the optical axis of the eye by less than one millimeter completely removes the corneal reflection.

The illuminating beam is preferably introduced into the optical path at the last possible location before the eye, e.g., by placing the beamsplitter right before the eye. Thus, back reflection from the lenses is avoided, as the only element between the beamsplitter and the retina is the cornea.

Even with the beamsplitter placed right before the eye, it is possible to adjust the focus of the illuminating beam and that of the exit beam by the use of the same element. One way to do so is to provide a folded optical path with mirrors mounted on a slide. The mirrors are disposed in the path of the illuminating beam before it reaches the beamsplitter and in the path of the exit beam. Thus, movement of the slide focuses both beams.

The light source can be moved in a direction perpendicular (or, more generally, non-parallel) to the direction of its output as needed to accommodate the eyes of different patients.

The present invention has utility in any procedure involving wavefront sensing of the eye or otherwise involving illumination of the retina. Such procedures include, but are not limited to, autorefraction, design of contact or intraocular lenses, refractive surgery and retinal imaging with adaptive optics. While it is contemplated that the present invention will be used with the human eye, veterinary or even non-eye-related applications can be developed as well.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

Figure 1:
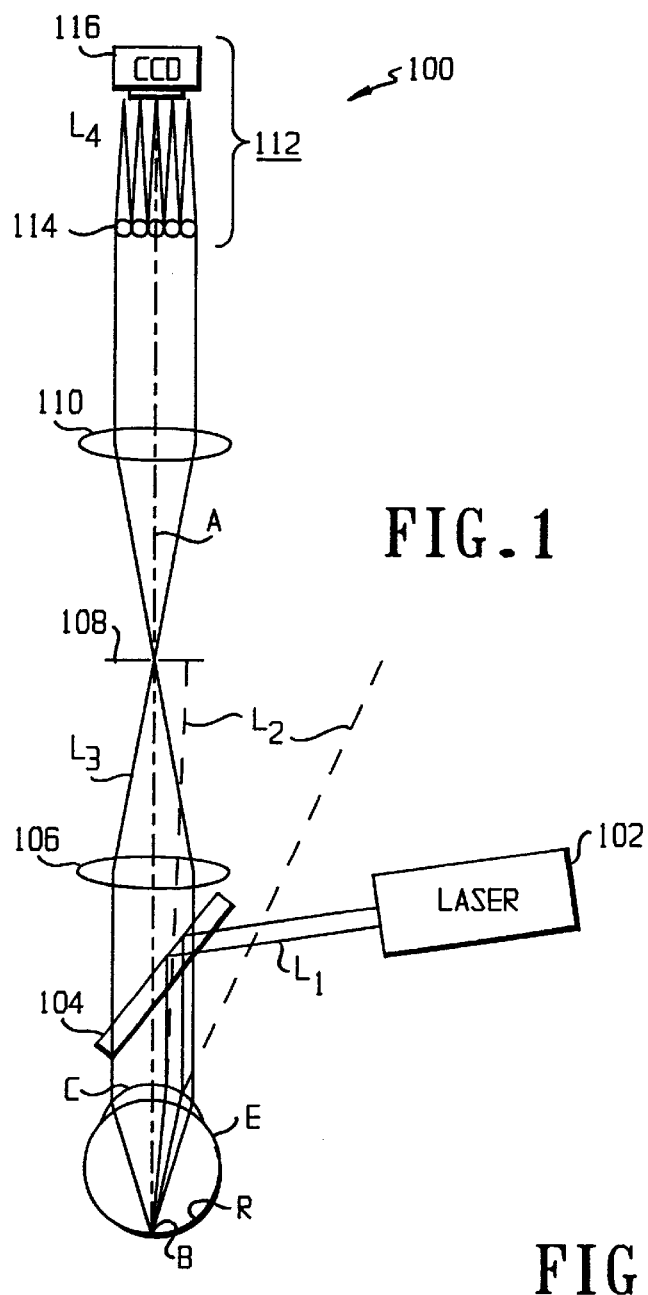
FIG. 1 is a schematic diagram showing the basic optical concepts implemented in a preferred embodiment of the invention.

FIG. 1 shows an overview of a basic system 100 for illuminating the retina of the patient's eye E and will be used to explain the optical principles implemented in the preferred embodiment. A laser light source 102, such as a laser diode, emits a beam of light $L_1$ toward a beamsplitter 104, which can be a parallel-plate beamsplitter, a thick-plate beamsplitter, a prism beamsplitter, a half-silvered mirror, or another suitable beamsplitter. The beamsplitter 104 is preferably 90% tmasmissive and 10% reflective, although other ratios could be used as needed. The laser light source 102 and the beamsplitter 104 are positioned such that the light $L_1$ impinges on the eye E off of the optical axis A of the eye E. Thus, a light beam $L_2$ reflected from the cornea C of the eye E is reflected off of the optical axis A. The remaining light forms a laser beacon B on the retina R of the eye E. Because of the optics of the eye E, a light beam $L_3$ reflected from the retina R of the eye E exits the eye E and passes through the beamsplitter 104. The light beam $L_3$ then passes through a lens 106, a stop 108 which passes the light beam $L_3$ reflected from the retina while blocking the light beam $L_2$ reflected from the cornea, and a lens 110 to a Hartmann-Shack detector 112. As known in the art, the detector 112 includes a lenslet array 114 to focus the light beam $L_3$ as an array of light spots $L_4$ onto a CCD or other suitable two-dimensional detector 116.

Figure 4:
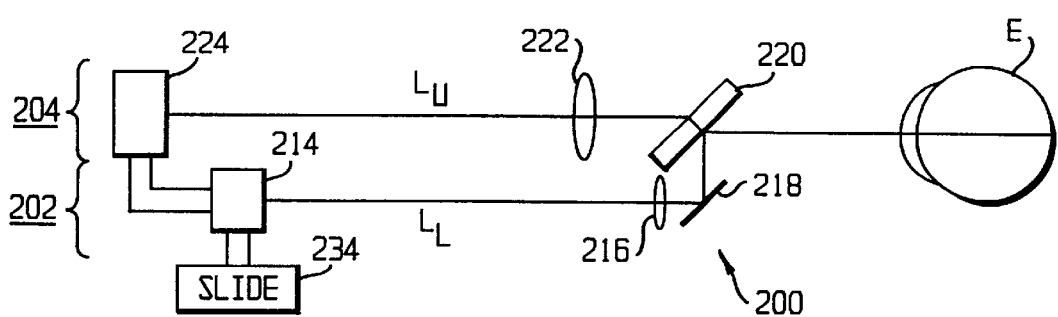
FIGS. 2–4 are schematic diagrams showing an arrangement of optical elements in a wavefront sensor according to the preferred embodiment.
Figure 2:
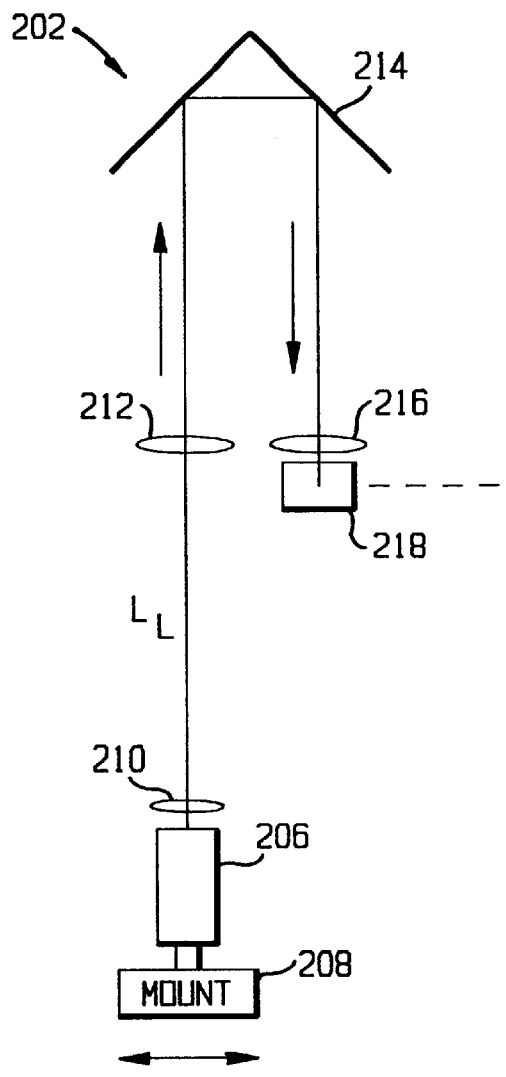
Figure 3:
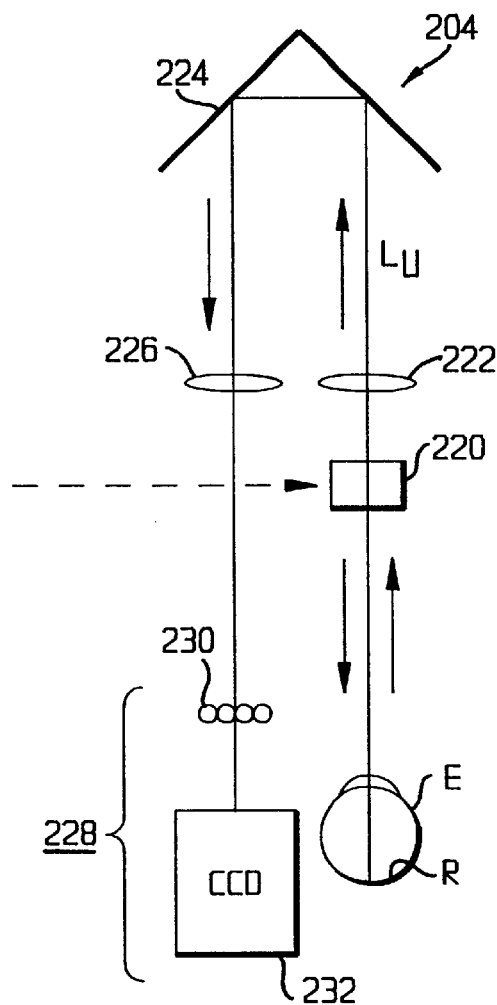

FIGS. 2–4 show a second-generation system 200 using the optical principles just explained with reference to FIG. 1. FIG. 2 shows a lower level 202 of the system 200 as seen from above, while FIG. 3 shows an upper level 204 of the system 200 as seen from above, and FIG. 4 shows both levels 202, 204 of the system 200 as seen from the right.

In the lower level 202, as shown in FIG. 2, a laser diode 206 is mounted on a mount 208 for horizontal positioning. The purpose of such positioning will be explained below. A light beam emitted from the diode 206 follows a lower-level light path designated generally as $L_L$ through lenses 210 and 212. The light beam is retroreflected by a corner mirror 214 and passes through a lens 216 to a mirror 218 which reflects the light beam upward.

In the upper level 204, as shown in FIG. 3, a parallel-plate beamsplitter 220 receives the light beam reflected upward by the mirror 218 and directs that light beam along an upper-level light path designated generally as $L_U$. The path $L_U$ is shown in greatly simplified form; the above discussion of FIG. 1 will provide those skilled in the art with an understanding of the requirements for the true optical path. The light beam illuminates the eye E in the manner explained above with reference to FIG. 1. A retinal reflection light beam reflected by the retina R of the eye E travels back through the beamsplitter 220 and a lens 222. The retinal reflection light beam is then retroreflected by a corner mirror 224 through a lens 226 to a Hartmann-Shack detector 228 which includes a lenslet array 230 and a CCD detector 232. Of course, a stop can be included at an appropriate location along the light path $L_U$, e.g., at the focus of the lens 222. Depending on the setup, a single mirror can be used to replace the mirrors 214 and 224.

The diameter of the incident light beam is a suitable value, e.g., 1.5 mm. The small diameter increases the depth of focus on the retina, thus relaxing the requirement to focus the light on the patient accurately.

The small diameter also ensures that the spot on the retina will be diffraction-limited. The entry beam should be no smaller than approximately the diameter of a lenslet in the lenslet array. Otherwise, diffraction in the entering beam will significantly blur the spots on the CCD.

The entry beam is displaced in the pupil from the corneal pole by a distance of more than one-half the diameter of the beam to separate the corneal and retinal reflections and thereby to avoid the effects of corneal reflection and is preferably displaced by about 1 mm. The distance may vary from subject to subject and can be less than 1 mm because of the small entrance beam diameter. The distance can be varied with the mount 208, which translates the diode 206 and its collimating optics by a small amount. The ability to translate the diode 206 and its optics by up to 1 mm suffices. The reflected light from the cornea is diverged and collimated by the lens 222, so that it can be blocked by a stop placed at the focus of the lens 222 or by another suitable optical element.

Back reflections from other optical components can be avoided by placing the beamsplitter 220 in the last possible place, just before the eye E. That arrangement allows the illuminating beam to avoid the other optical elements, since the only thing between the beamsplitter 220 and the retina R is the,cornea C.

The usual reflections from the beamsplitter can be avoided by using a rotated beamsplitter cube or a thick-plate beamsplitter. It is not necessary to subtract an image without the eye in place from an image with the eye in place to remove stray light, as was often required in the prior art.

As shown in FIG. 4, the optical path length of the system 200 can be varied by coupling the mirrors 214 and 224 to a slide mechanism 234 so that the mirrors 214 and 224 can be moved as a single rigid body. The mirrors 214 and 224 are displaced from each other axially. The movement of the slide mechanism 234 by a distance x changes the optical path length of each level 202, 204 by a distance 2x and of the system 200 as a whole by a distance 4x.

Another advantage of a slide mechanism is that it allows the entering beam to be focused on the retina at the same time and with the same device with which the exit beam is focused on the CCD array, namely, the slide 234 bearing the mirrors 214 and 224. Since the mirror 214 is in the path of the illuminating beam before that beam reaches the beamsplitter 220 and the mirror 224 is in the path of the exit beam, movement of the slide 234 changes the path lengths of both beams and thereby allows adjustment of the focus of both beams. The slide 234 thus provides economy and convenience.

Double slide mechanisms could be implemented in the system 200. For example, another mirror (not shown) could be placed opposite the mirrors 214 and 224 to cause the light beam to make another pass through the system. With that arrangement, movement of the slide mechanism 234 by a distance x would change the total optical path length by a distance 8x.

Figure 5:
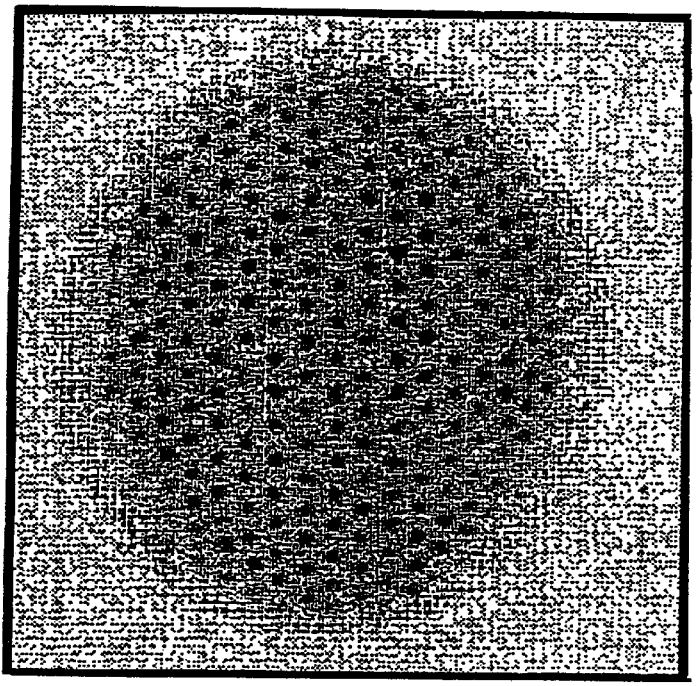
FIGS. 5 and 6 show experimental results obtained according to the preferred embodiment and the prior art, respectively.
Figure 6:
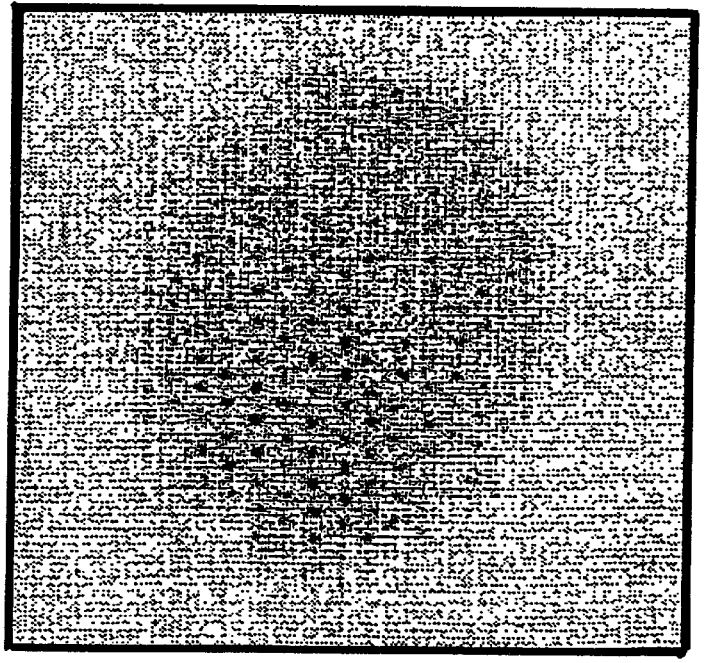

Experimental results are shown in FIGS. 5 and 6. FIG. 5 shows a result taken with off-axis illumination according to the present invention, with no polarizing beamsplitter and with an SLD light source emitting a wavelength $\lambda$=790 mm. FIG. 6 shows a result taken with conventional on-axis illumination, with a polarizing beamsplitter but without a $\lambda$/4 plate, and with a He—Ne laser light source emitting a wavelength $\lambda$=633 nm. Both results are taken under the following conditions: paralyzed accommodation for a pupil diameter of 6.7 mm, an exposure time of 500 ms, an entrance laser power of 10 $\mu$W and an entrance beam diameter of 1.5 mm.

A comparison of FIGS. 5 and 6 shows that the present invention provides a great improvement in light throughput and also in spot quality. The spot pattern shown in FIG. 5 has much better intensity uniformity than that of FIG. 6 and has an average spot intensity four times higher than that of FIG. 6. In fact, in both respects, the spot pattern of FIG. 5 is comparable to that obtained with a polarizing beamsplitter and a $\lambda$/4 plate, without the drawbacks of that technique. The single non-polarizing beamsplitter 220, which can be a parallel plate beamsplitter or the like, is less expensive than the optics required for the polarizing techniques of the prior art, with or without a $\lambda$/4 plate. The use of a beamsplitter with a ratio of transmittance to reflection greater than one further increases the light available.

The present invention offers many advantages. The deleterious effects of back reflections in the eye and other optics are avoided, thereby making the instrument more robust and the software to operate it simpler. The quality of the spot images is not degraded by polarization effects, so that accuracy is improved. The throughput is higher than that of the prior art, so that a greater signal can be achieved for the same level of illumination and thus the same level of patient comfort and safety. Alternatively, the same signal as in the prior art can be achieved with reduced illuminating light intensity and thus improved patient comfort and safety. With a sufficiently bright diode, the ratio of transmission to reflection of the plate beamsplitter can be chosen to transmit almost all of the light from the retina to the CCD array. Since no polarizing optics are required, the cost is reduced.

While a preferred embodiment has been set forth above, those skilled in the art who have reviewed the present disclosure will recognize that other embodiments can be realized within the scope of the invention. For example, the optical path can have additional folds for improved path length and compactness, and a fixation target and pupil camera can be added. Also, the light source can be positioned in any manner which spatially separates the retinal and corneal reflections, e.g., by selection of an appropriate angle of incidence. Therefore, the present invention should be construed as limited only by the appended claims.

What is claimed is:

1. A method of illuminating a retina of an eye, the method comprising:

positioning a light source relative to the eye such that light from the light source reflected from a cornea of the eye travels along a first path and such that light from the light source reflected from the retina travels along a second path which is spatially separated from the first path;

illuminating the retina with the light source;

receiving the light reflected from the retina in a detector; and detecting a wavefront aberration of the eye with the detector.

2. The method of claim 1, further comprising providing a stop to pass the light traveling along the second path and to block the light traveling along the first path.

3. The method of claim 1, wherein the light source is a laser diode.

4. The method of claim 1, wherein:

the light source emits a light beam; and said step of positioning comprises positioning the light source such that the light beam is incident on the eye off of an optical axis of the eye.

5. The method of claim 4, wherein the light source is positioned off of the optical axis by a distance great enough to allow separation between the light reflected from the cornea and the light reflected from the retina.

6. The method of claim 1, wherein the detector is a Hartman-Shack detector.

7. The method of claim 1, wherein said step of illuminating comprises directing light from the light source to the eye with a non-polarizing beamsplitter.

8. A method of illuminating a retina of an eye, the method comprising:

positioning a light source relative to the eye such that light from the light source reflected from a cornea of the eye travels along a first path and such that light from the light source reflected from the retina travels along a second path which is spatially separated from the first path; and illuminating the retina with the light source;

wherein the step of illuminating comprises directing light from the light source to the eye with a non-polarizing cube beamsplitter.

9. The method of claim 7, wherein the non-polarizing beamsplitter is a plate beamsplitter.

10. A system for illuminating a retina of an eye, the system comprising:

a light source positioned relative to the eye such that light from the light source reflected from a cornea of the eye travels along a first path and such that light from the light source reflected from the retina travels along a second path which is spatially separated from the first path; and an optical element for receiving the light traveling along the second path;

wherein the optical element comprises a detector, positioned to receive the light reflected from the retina, for detecting a wavefront aberration of the eye.

11. The system of claim 10, wherein the optical element comprises a stop for passing the light traveling along the second path and for blocking the light traveling along the first path.

12. The system of claim 10, wherein the light source is a laser diode.

13. The system of claim 10, wherein the light source emits a light beam and is positioned such that the light beam is incident on the eye off of an optical axis of the eye.

14. The system of claim 13, wherein the light source is positioned off of the optical axis by a distance great enough to allow separation between the light reflected from the cornea and the light reflected from the retina.

15. The system of claim 10, wherein the detector is a Hartmann-Shack detector.

16. The system of claim 10, further comprising a non-polarizing beamsplitter for directing light from the light source to the eye.

17. The system of claim 16, wherein the non-polarizing beamsplitter is a plate beamsplitter.

18. A system for illuminating a retina of an eye, the system comprising:

a light source positioned relative to the eye such that light from the light source reflected from a cornea of the eye travels along a first path and such that light from the light source reflected from the retina travels along a second path which is spatially separated from the first path;

an optical element for receiving the light traveling along the second path; and a non-polarizing cube beamsplitter for directing light from the light source to the eye.

19. A method of determining a wavefront aberration of an optical element, the method comprising:

positioning a light source relative to the optical element such that light from the light source reflected from a surface of the optical element travels along a first path and such that light from the light source transmitted through the optical element and reflected back through the optical element travels along a second path which is spatially separated from the first path;

illuminating the optical element with the light source;

receiving the light traveling along the second path with a detector; and detecting the wavefront aberration with the detector.

20. A system for determining a wavefront aberration of an optical element, the system comprising:

a light source positioned relative to the optical element such that light from the light source reflected from a surface of the optical element travels along a first path and such that light from the light source transmitted through the optical element and reflected back through the optical element travels along a second path which is spatially separated from the first path; and a detector for receiving the light traveling along the second path and for detecting the wavefront aberration.

* * * * *

UNITED STATES PATENT AND TRADEMARK OFFICE
CERTIFICATE OF CORRECTION

PATENT NO.     : 6,264,328 B1
DATED          : July 24, 2001
INVENTOR(S)    : David R. Williams et al.

It is certified that error appears in the above-identified patent and that said Letters Patent is hereby corrected as shown below:

<u>Column 1,</u>
Line 1, please insert -- This invention was made under a contract with the National Eye Institute of the United States Government under Grant No. R01 EY04367. The government has certain rights in this invention. --

Signed and Sealed this

Eighth Day of June, 2004

JON W. DUDAS
*Acting Director of the United States Patent and Trademark Office*